(12) United States Patent
Zhou et al.

(10) Patent No.: US 7,656,991 B2
(45) Date of Patent: Feb. 2, 2010

(54) IMAGE RECONSTRUCTION METHOD AND X-RAY CT APPARATUS

(75) Inventors: Yu Zhou, Beijing (CN); Wu Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 275 days.

(21) Appl. No.: 11/684,157

(22) Filed: Mar. 9, 2007

(65) Prior Publication Data

US 2007/0211846 A1    Sep. 13, 2007

(30) Foreign Application Priority Data

Mar. 10, 2006    (CN) ............ 200610073962

(51) Int. Cl.
  *A61B 6/03*    (2006.01)
  *H05G 1/60*    (2006.01)
(52) U.S. Cl. .......................... 378/4; 378/901
(58) Field of Classification Search .............. 378/4, 378/901
  See application file for complete search history.

(56) References Cited

U.S. PATENT DOCUMENTS

| | | | | |
|---|---|---|---|---|
| 5,483,567 A * | 1/1996 | Swerdloff | ............... | 378/4 |
| 5,909,476 A * | 6/1999 | Cheng et al. | ............... | 378/4 |
| 7,127,095 B2 | 10/2006 | El Fakhri et al. | | |
| 7,173,248 B2 | 2/2007 | Ross et al. | | |
| 7,206,441 B2 * | 4/2007 | Kohler | ............... | 382/131 |
| 7,251,306 B2 * | 7/2007 | Sauer et al. | ............... | 378/4 |
| 7,272,205 B2 * | 9/2007 | Thibault et al. | ............... | 378/4 |
| 2006/0013354 A1 * | 1/2006 | Heismann | ............... | 378/4 |
| 2006/0013355 A1 * | 1/2006 | Heismann | ............... | 378/4 |
| 2007/0040122 A1 | 2/2007 | Manjeshwar et al. | | |
| 2007/0201611 A1 * | 8/2007 | Pratx et al. | ............... | 378/4 |
| 2008/0025461 A1 * | 1/2008 | Foland et al. | ............... | 378/17 |
| 2008/0084962 A1 * | 4/2008 | Zhang et al. | ............... | 378/57 |
| 2008/0267477 A1 * | 10/2008 | Conti et al. | ............... | 382/131 |

OTHER PUBLICATIONS

H. Malcolm Hudson and Richard S. Larkin, "Accelerated Image Reconstruction Using Ordered Subsets of Projection data." IEEE Transactions on Medical Imaging, vol. 13, No. 4, 1994, p. 601-609.*
A. Rahmim et al.; Study of a Convergent Subsetized List-mode EM Reconstruction Algorithm; 2004 IEEE ; pp. 3978-3982.

* cited by examiner

*Primary Examiner*—Allen C. Ho
(74) *Attorney, Agent, or Firm*—Armstrong Teasdale LLP

(57) ABSTRACT

The present invention is intended to provide an image reconstruction method based on an iterative reconstruction technique and characterized by a short image reconstruction time, a small memory capacity, and high image quality. The image reconstruction method comprises the steps of: constructing a system model that has a plurality of concentric rings each segmented into a plurality of sectors; constructing a system matrix associated with one view, by using some of all the sectors constituting the system model, the some of all sectors being located on respective projection lines concerning the one view; creating a system matrix associated with another view, by transforming the system matrix associated with the one view; reconstructing an image through iterative reconstruction by using the system matrix and projection data; and transforming the image into an image composed of rectangular pixels.

9 Claims, 9 Drawing Sheets

View 1

View 2

| System Matrix | Projection Line | | Projection Stripe | |
|---|---|---|---|---|
| System Model | Conventional Model | Model in Accordance with Present Invention | Conventional Model | Model in Accordance with Present Invention |
| Reconstruction Time (S) | 350 | 85 | 1750 | 90 |
| Time Ratio | 4.1 | | 19.4 | |

Profile Plot Images

——— Round
—··— Rectangle
------ Phantom

IMAGE RECONSTRUCTION METHOD AND X-RAY CT APPARATUS

CROSS REFERENCE TO RELATED APPLICATIONS

This application claims the benefit of Chinese Application No. 200610073962.5 filed Mar. 10, 2006, which is hereby incorporated by reference in its entirety.

BACKGROUND OF THE INVENTION

The present invention relates to an image reconstruction method and an X-ray computed tomography (CT) system, or more particularly, an image reconstruction method based on an iterative reconstruction technique and an X-ray CT apparatus that performs the image reconstruction.

Iterative reconstruction is known as one of techniques for reconstructing an image on the basis of projection data produced by an X-ray CT apparatus or a positron emission tomography (PET) system.

The iterative reconstruction is such that an estimated distribution of coefficients in a system model is sequentially corrected until projection data produced from the estimated distribution of coefficients will agree with projection data produced from actual measurement. The iterative reconstruction may be referred to as statistical reconstruction. Typical examples of the image reconstruction technique include an ordered subsets expectation maximization (OSEM) technique (refer to, for example, Non-patent Document 1).

[Non-Patent Document 1] "Study of a Convergent Subsetized List-mode EM Reconstruction Algorithm" by A. Rahmin, T. J. Ruth, and V. Sossi (Nuclear Science Symposium Conference Record 2004 IEEE, Oct. 2004, Vol. 6, pp. 3978-3982)

According to the foregoing technique, a spatial array of coefficients formed like a rectangular lattice is adopted as a system model. A system matrix for use in reconstructing an image of the system model has a complex structure and includes an enormous amount of data. The calculation of the system matrix is a large load to be imposed on a computer.

As shown in FIG. 15(a), when a stored matrix having been calculated in advance is used, a large memory capacity is required. If a system matrix is, as shown in FIG. 15(b), calculated at every time of image reconstruction, an image reconstruction time gets longer. If the system matrix is simplified in order to shorten the image reconstruction time, image quality deteriorates.

SUMMARY OF THE INVENTION

Therefore, an object of the present invention is to provide an image reconstruction method based on an iterative reconstruction technique and characterized by a short image reconstruction time, a small memory capacity, and high image quality, and an X-ray CT apparatus that performs such image reconstruction.

For accomplishing the above object, according to the first aspect of the present invention, there is provided an image reconstruction method characterized in that: a system model has a plurality of concentric rings each segmented into a plurality of sectors; a system matrix to be associated with one view is constructed with some of all the sectors constituting the system model, the some of all the sectors being located on projection lines concerning the one view; the system matrix associated with the one view is transformed in order to produce a system matrix to be associated with another view; the system matrix and projection data are used to reconstruct an image through interactive reconstruction; and the image is transformed into an image composed of rectangular pixels.

For accomplishing the foregoing object, according to the second aspect of the present invention, there is provided an X-ray CT apparatus including data acquisition equipment that scans a subject with X-rays so as to acquire projection data, and image reconstruction equipment that reconstructs an image on the basis of the acquired projection data. The image reconstruction equipment includes: a system model construction means for constructing a system model that has a plurality of concentric rings each segmented into a plurality of sectors; a system matrix construction means for constructing a system matrix associated with one view, by using some of all the sectors constituting the system model, the some of all the sectors being located on respective projection lines concerning the one view; a system matrix creation means for creating a system matrix associated with another view, by transforming the system matrix associated with the one view; an image reconstruction means that reconstructs an image through iterative reconstruction by using the system matrix and projection data; and a transformation means for transforming the image into an image composed of rectangular pixels.

Preferably, each of elements constituting the system matrix is a length of a projection line falling within each sector so that the system matrix can be simplified.

Preferably, each of elements constituting the system matrix is a partial area of a projection stripe falling within each sector so that the system matrix can be formed precisely.

Preferably, the partial area is a normalized area so that the element can be standardized.

Preferably, a system matrix to be associated with another view is created at each time of iteration so that the system matrix can be created timely.

Preferably, an ordered subsets expectation maximization (OSEM) technique is adopted as the iterative reconstruction technique so that image reconstruction can be achieved properly.

Preferably, transformation to an image composed of rectangular pixels is achieved through bilinear interpolation so that the transformation can be achieved properly.

Preferably, the projection lines express fan-beam X-rays so that a matrix will be well associated with projection data provided by the fan-beam X-rays.

Preferably, the projection lines express parallel-beam X-rays so that a matrix will be well associated with projection data provided by the parallel-beam X-rays.

The present invention can provide an image reconstruction method based on an iterative reconstruction technique and an X-ray CT apparatus that performs the image reconstruction. Herein, a system model is constructed to have a plurality of concentric rings each segmented into a plurality of sectors. A system matrix to be associated with one view is constructed using part of all the sectors constituting the system matrix which is located on respective projection lines concerning the one view. The system matrix associated with the one view is transformed in order to create a system matrix to be associated with another view. The system matrix and projection data are used to reconstruct an image through iterative reconstruction. The image is transformed into an image composed of rectangular pixels. This results in a short image reconstruction time, a small memory capacity, and high image quality.

Further objects and advantages of the present invention will be apparent from the following description of the preferred embodiments of the invention as illustrated in the accompanying drawings.

BRIEF DESCRIPTION OF THE DRAWINGS

FIG. 14a1, 14a2, 14a3, 14b1, 14b2, 14b3, 14c1, 14c2, and 14c3 are halftone photographs showing the reconstructed image produced according to the method in accordance with the present invention in comparison with a reconstructed image produced according to a filtered back projection (FBP) technique.

DETAILED DESCRIPTION OF THE INVENTION

Figure 1:
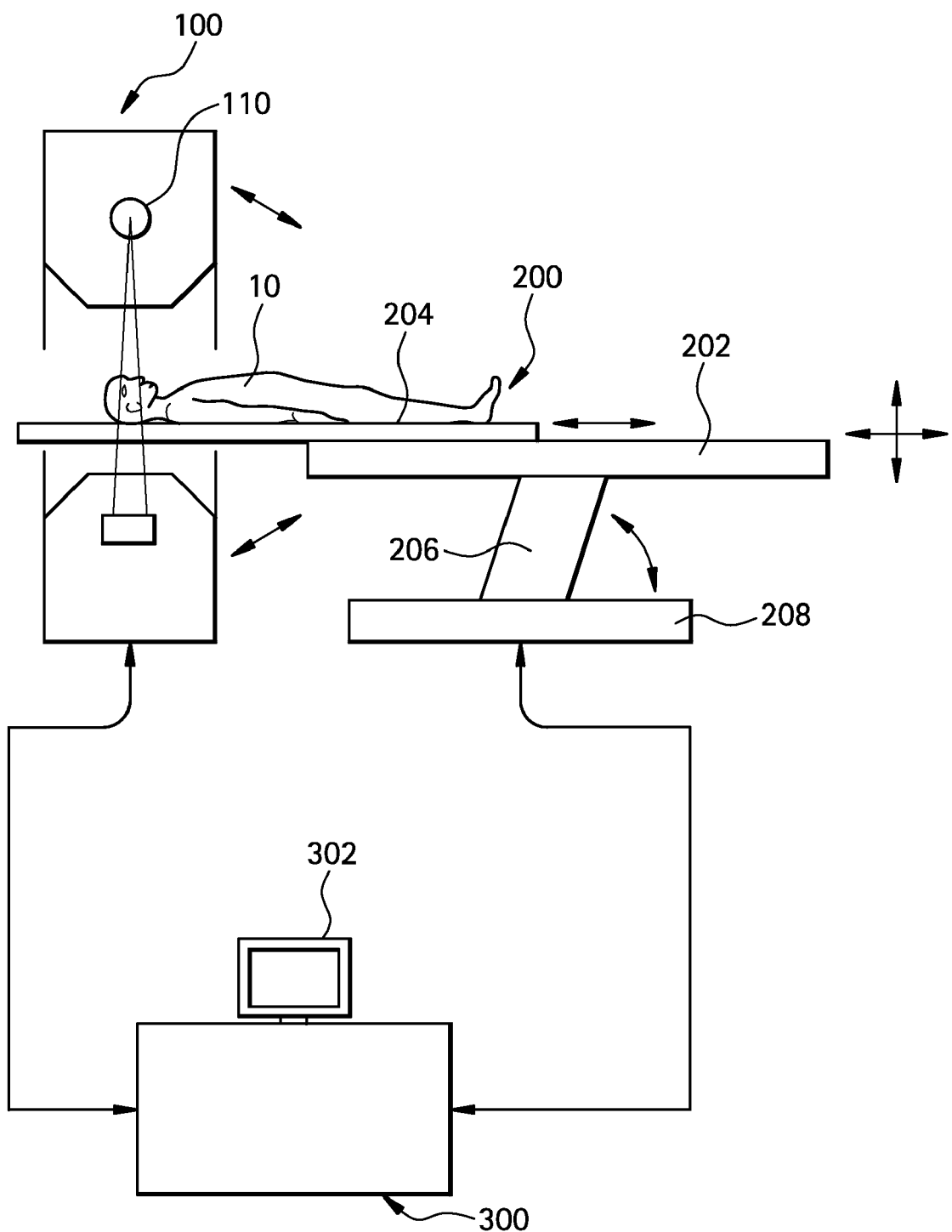
FIG. 1 shows the configuration of an X-ray CT apparatus that is an example of the best mode for implementing the present invention.

Referring to drawings, the best mode for implementing the present invention will be described below. Noted is that the present invention is not limited to the best mode for implementing the present invention. FIG. 1 illustrates the configuration of an X-ray CT apparatus. The X-ray CT apparatus is an example of the best mode for implementing the present invention. The configuration of the X-ray CT apparatus is an example of the best mode for implementing the present invention in an X-ray CT apparatus.

The X-ray CT apparatus includes a gantry 100, a table 200, and an operator console 300. The gantry 100 uses X-irradiation/detection equipment 110 to scan a subject 10 who lies down on the table 200, thus acquires transmitted X-ray signals carrying a plurality of views (projection data), and transfers the signals to the operator console 300. The gantry 100 is an example of data acquisition equipment included in the present invention.

The operator console 300 uses a built-in computer to reconstruct an image on the basis of the projection data received from the gantry 100, and displays the image on a display 302. The operator console 300 is an example of image reconstruction equipment included in the present invention.

The operator console 300 controls the operations of the gantry 100 and table 200 respectively. The gantry 100 scans a subject according to predetermined scanning conditions under the control of the operator console 300. The table 200 positions the subject 10 so that a predetermined region of the subject will be scanned. The positioning is achieved when a built-in alignment mechanism adjusts the height of a tabletop 202 and a horizontal distance by which a cradle 204 on the tabletop is moved.

A scan is performed with the cradle 204 at a halt, whereby an axial scan is achieved. A plurality of scans is continuously performed with the cradle 204 continuously moved, whereby a helical scan is achieved. The cradle 204 is intermittently moved and a scan is performed every time the cradle 204 is halted, whereby a cluster scan is achieved.

The height of the tabletop 202 is adjusted by swinging a columnar support 206 with the root of the columnar support at a base 208 as a center. With the swing of the columnar support 206, the tabletop 202 is displaced vertically and horizontally. The cradle 204 is moved horizontally on the tabletop 202, whereby the horizontal displacement of the tabletop 202 is canceled out. Depending on scanning conditions, a scan is performed with the gantry 100 tilted. The gantry 100 is tilted by a built-in tilting mechanism.

Figure 2:
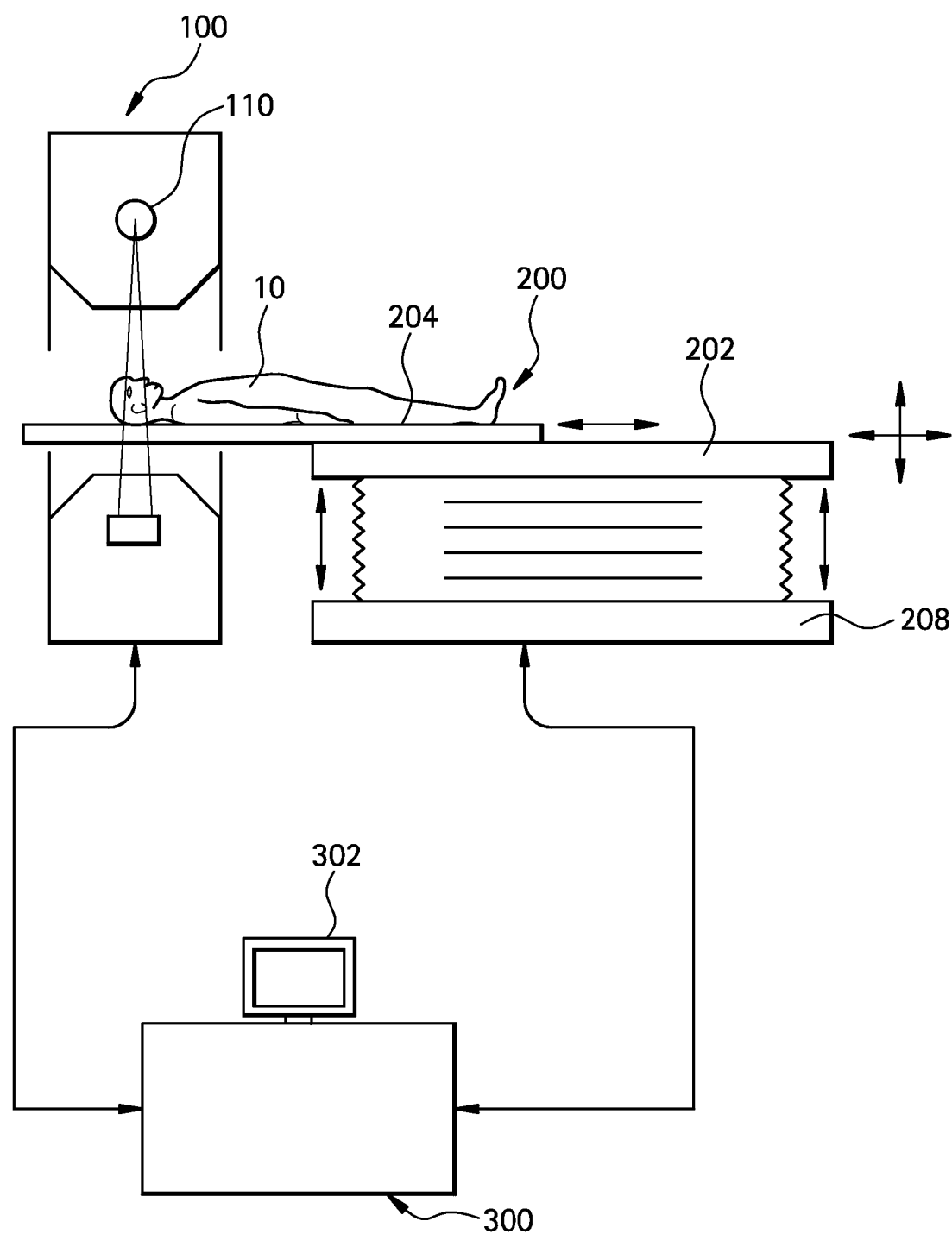
FIG. 2 shows the configuration of the X-ray CT apparatus that is an example of the best mode for implementing the present invention.

The table 200 may be, as shown in FIG. 2, of a type having the tabletop 202 lifted or lowered relative to the base 208. The tabletop 202 is lifted or lowered by a built-in lifting/lowering mechanism. In this type of table 200, the lifting or lowering is not accompanied by the horizontal movement of the tabletop 202.

Figure 3:
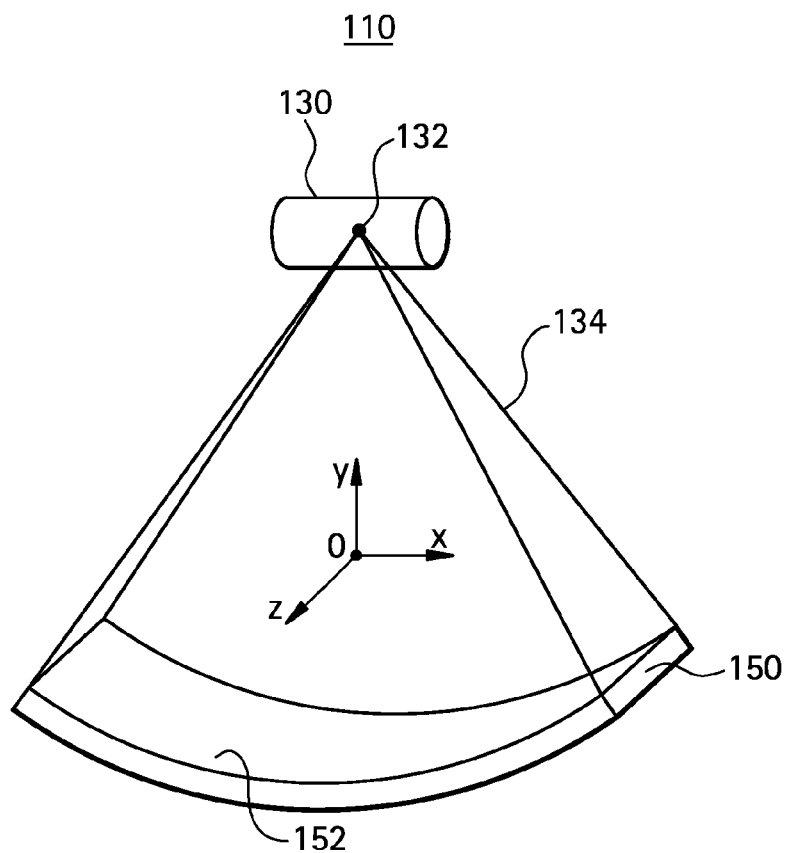
FIG. 3 shows the configuration of X-ray irradiation/detection equipment.

FIG. 3 illustrates the configuration of the X-irradiation/detection equipment 110. In the X-irradiation/detection equipment 110, an X-ray detector 150 detects X-rays 134 irradiated from a focal spot 132 in an X-ray tube 130.

The X-rays 134 are reshaped by a collimator that is not shown to be a laterally symmetrical cone beam or fan beam. The X-ray detector 150 has an X-ray incidence surface 152 that spread two-dimensionally along with the fanning out of the X-rays. The X-ray incidence surface 152 is curved in the form of part of a cylinder. The center axis of the cylinder passes through the focal spot 132.

The X-irradiation/detection equipment 110 rotates about a center axis passing through a radiographic center, that is, an isocenter O. The center axis extends parallel to the center axis of the partial cylinder formed by the X-ray detector 150.

Assume that the direction of the center axis of rotation is a z direction, the direction linking the isocenter O and the focal spot 132 is a y direction, and the direction perpendicular to the z and y directions is an x direction. The x, y, and z axes serve as three axes of a rotating coordinate system that rotates with the z axis as a center axis.

Figure 4:
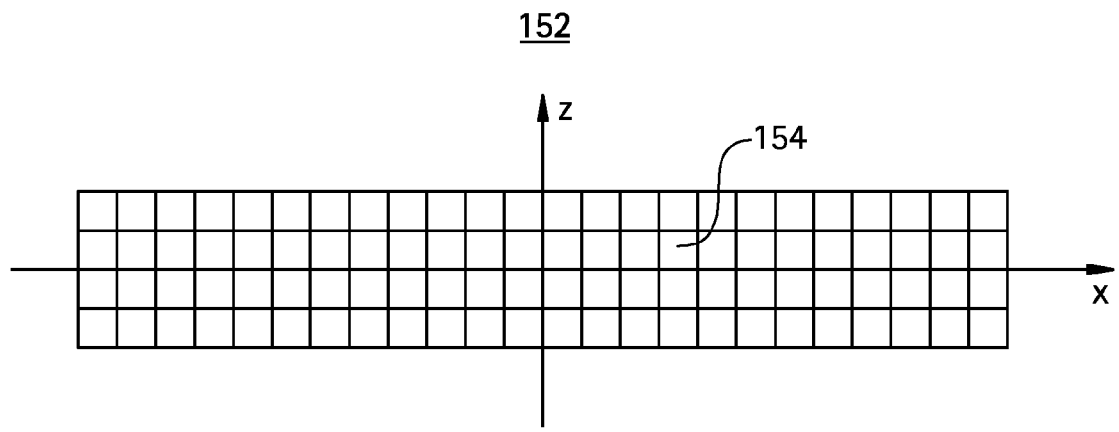
FIG. 4 shows the structure of an X-ray incidence surface of an X-ray detector.

FIG. 4 is a plan view illustrating the X-ray incidence surface 152 of the X-ray detector 150. The X-ray incidence surface 152 has detector cells 154 two-dimensionally arrayed in the x and z directions. In other words, the X-ray incidence surface 152 is formed with the two-dimensional array of the detector cells 154. When fan-beam X-rays are employed, the X-ray incidence surface 152 may be formed with a one-dimensional array of the detector cells 154.

Each of the detector cells 154 serves as a detection channel in the X-ray detector 150. Consequently, the X-ray detector 150 is a multi-channel X-ray detector. Each of the detector cells 154 is composed of, for example, a scintillator and a photodiode.

Figure 5:
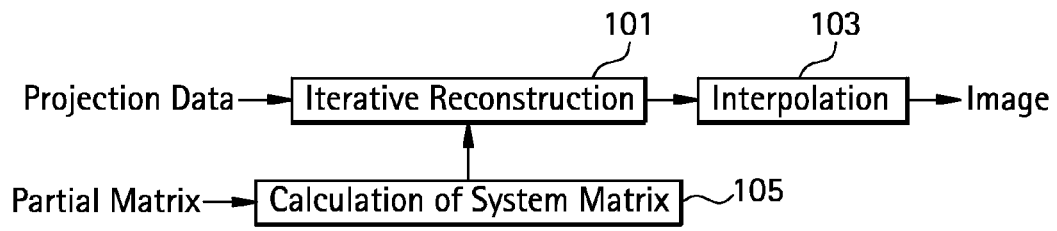
FIG. 5 outlines a process that is an example of the best mode for implementing the present invention.

FIG. 5 outlines an image reconstruction process to be executed in the operator console 300. The process is an example of the best mode for implementing an image reconstruction method in accordance with the present invention. The process is executed by a built-in computer.

As mentioned in FIG. 5, iterative reconstruction is performed at step 101. At step 103, interpolation is performed in order to display an image. The iterative reconstruction of step 101 is performed based on, for example, the ordered subsets expectation maximization (OSEM) technique. Consequently, image reconstruction can be achieved properly.

The iterative reconstruction may not be performed based on the OSEM technique but may be performed based on a multiplicative algebraic reconstruction (MART) technique or a paraboloidal surrogate coordinate descent (PSCD) technique. The image reconstruction based on the OSEM technique will be described below. Noted is that the same applies to the image reconstruction based on the MART or PSCD technique.

For the iterative reconstruction, projection data and a system matrix calculated at step 105 are employed. A partial matrix stored in advance is used to calculate the system matrix.

Figure 6:
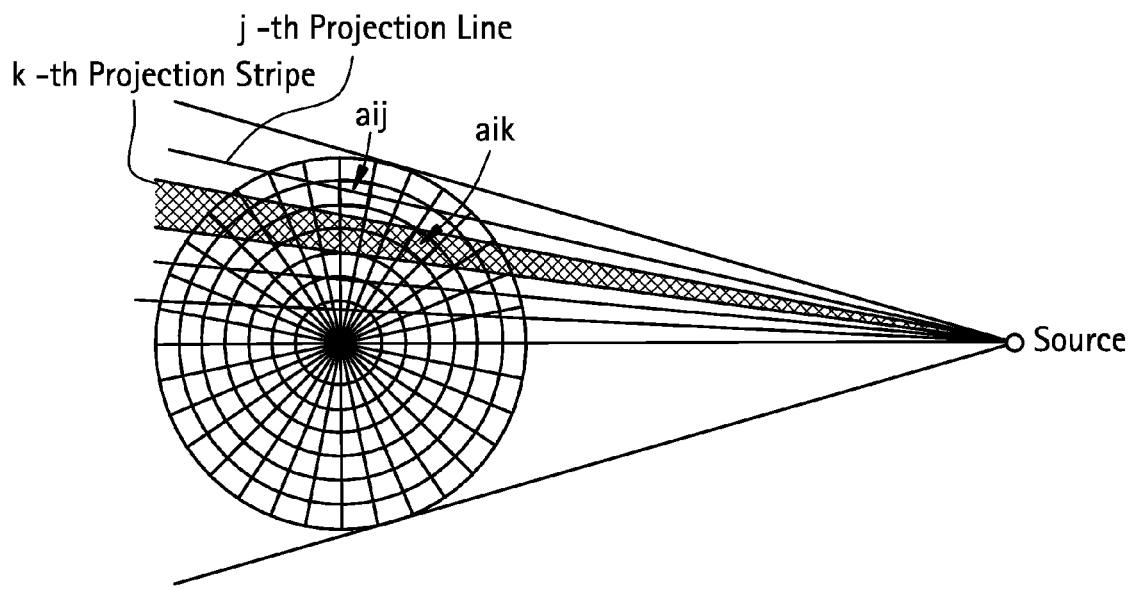
FIG. 6 shows a system model and projection lines.

The partial matrix will be described below. Beforehand, a system model with which the partial matrix is concerned will be described. FIG. 6 illustrates the system model. As illustrated in FIG. 6, the system model has a plurality of concentric rings.

Each of the rings is segmented into equiangular sectors. An angle in units of which each ring is segmented is equal to an angle step of view, or an integral multiple thereof. The number of sectors into which each ring is segmented need not be the same among all rings. The number of sectors into which the outermost ring is segmented may be the largest. In this case, the lengths of respective sectors become nearly uniform over an entire system model. Moreover, the widths of respective rings need not be the same but may vary.

A plurality of projection lines extending radially from a source expresses X-rays that provide projection data constituting one view (i denotes a view number) of the system model. The projection lines express respective X-rays of, for example, fan-beam X-rays. A projection line expressing a center X-ray of the fan-beam X-rays shall pass through the center of the system model and be perpendicular to one of the radii of the rings. Using the projection lines, a matrix can be well associated with the projection data provided by the fan-beam X-rays.

When parallel-beam X-rays are substituted for the fan-beam X-rays, the plurality of projection lines extends parallel to one another, and is perpendicular to one of the radii of the rings. Using the projection lines, a matrix can be well associated with projection data provided by the parallel-beam X-rays. The description will proceed by taking a case, where the radial projection lines are employed, for instance. Noted is that the same applies to a case where the parallel projection lines are employed.

The projection lines pass through specific sectors of the system model. One sector (highlighted) through which the j-th projection line passes shall be focused. A partial matrix is defined as a set of such sectors through which all projection lines pass while expressing X-rays that provide one view. The partial matrix may be regarded as a system matrix associated with a view i. A set of partial matrices associated with all views is regarded as a system matrix. Hereinafter, the partial matrix may be simply called a matrix.

Each of elements constituting a system matrix shall be a length aij of a projection line j falling within each sector. This definition simplifies the system matrix.

Each of the elements may be defined as a partial area aik of a projection stripe k falling within each sector (highlighted). This definition realizes a precise system matrix.

Figure 7:
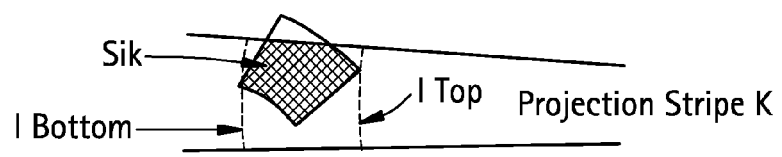
FIG. 7 shows part of a projection stripe.

FIG. 7 shows the partial area in detail. A hatched part indicates the partial area of a projection stripe falling within a sector. The size of the area is expressed with an area Sik normalized as follows:

$$aik = Sik/((l_{top}+l_{bottom})/2)$$ Formula 1

Herein, ltop and lbottom denote the lengths of the arcs in a stripe k on the side of the source and an opposite side which define a sector. Thus, each element is standardized.

Figure 8A:
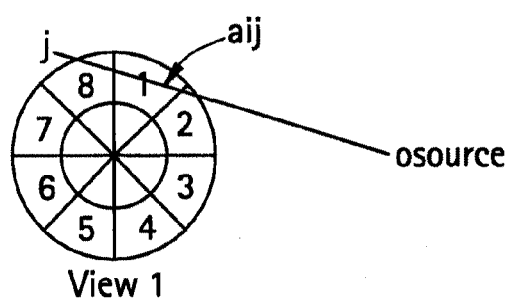
FIGS. 8a and 8b show a system model and a projection line in association with two successive views.
Figure 8B:
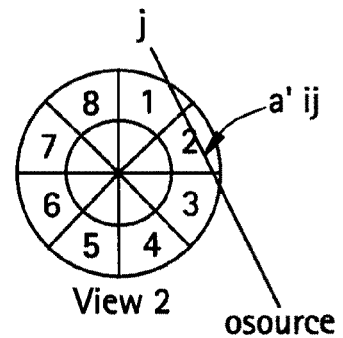

Referring to FIG. 8, the property of a partial matrix will be described. FIG. 8(a) and FIG. 8(b) show scenes where a projection line j that passes through a system model expresses one of X-rays providing either of two successive views 1 and 2. Herein, for brevity's sake, the number of views is eight in total.

As shown in FIG. 8(a) and FIG. 8(b), the projection line j passes through a sector 1 while expressing one of X-rays that provide the view 1, while the projection line j passes through a sector 2 while expressing one of X-rays that provide the view 2. Since an angle in units of which each ring of a system model is segmented into sectors is equal to the angle step of the view, the positions of the sectors 1 and 2 through which the projection line j passes while expressing one of X-rays that provide the view 1 or 2 are identical to each other.

Consequently, the scene where the projection line j passes through the sector 2 while expressing one of X-rays that provide the view 2 is identical to the scene where the projection line j passes through the sector 1 while expressing one of X-rays that provide the view 1. Consequently, an element aij included in the partial matrix associated with the view 2 assumes the same value as an element aij included in the partial matrix associated with the view 1.

The same relationship is established between all projection lines expressing X-rays that provide the view 1 and all projection lines expressing X-rays that provide the view 2, and also established among all other projection lines expressing X-rays that provide a view 3, those expressing X-rays that provide a view 4, those expressing X-rays that provide a view 5, those expressing X-rays that provide a view 6, those expressing X-rays that provide a view 7, and those expressing X-rays that provide a view 8. Consequently, the structures of partial matrices associated with all the views are the same as one another except view numbers. Once a partial matrix associated with one view is calculated and stored in advance, therefore, all the remaining partial matrices can be created through transformation of the stored partial matrix. The same applies to a case where a partial area of a projection stripe falling within each sector is regarded as an element.

Figure 9:
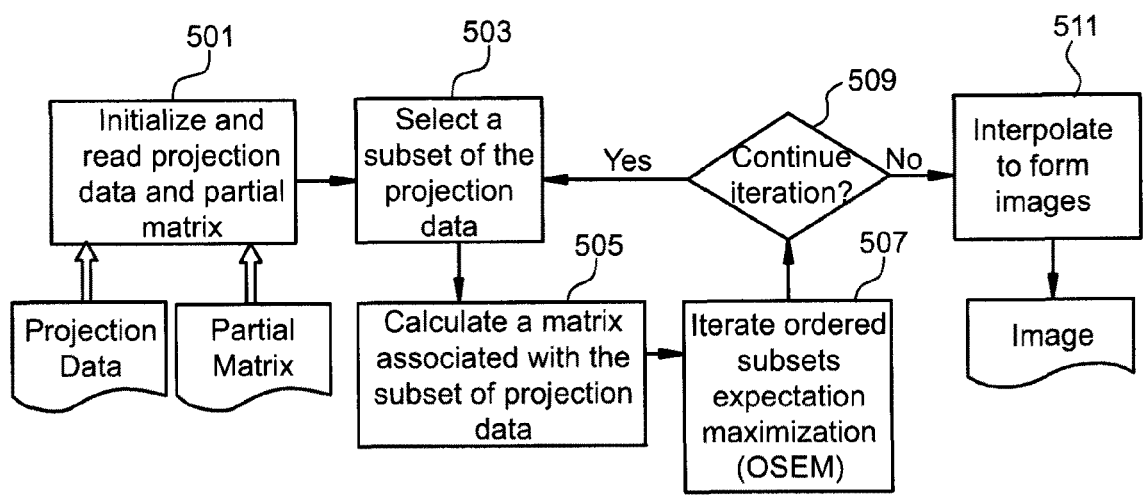
FIG. 9 describes a process that is an example of the best mode for implementing the present invention.

FIG. 9 details an image reconstruction process. As described in FIG. 9, initialization and reading of projection data and a matrix are performed at step 501. The matrix is calculated and stored in a memory in advance. The matrix is a partial matrix, or in other words, a system matrix associated with one view. The calculation is not a large load imposed on a computer, and the storage of the matrix does not consume a large memory capacity.

At step 503, a subset of projection data is selected. At step 505, a matrix to be associated with the subset is calculated. The matrix to be associated with the subset is calculated from the partial matrix read from the memory. The calculation includes simple transformation and therefore imposes only a small load on the computer.

At step 507, ordered subsets expectation maximization (OSEM) is iterated once. At step 509, whether the iteration is continued is determined. If the iteration is recognized to be necessary, control is returned to step 503. A subset of projection data is selected at step 503, a matrix is calculated at step 505, and OSEM is iterated at step 507. Thus, an image is reconstructed through iterative reconstruction. Since a matrix to be associated with a subset is calculated at every time of iteration of OSEM, a system matrix can be created timely.

Figures 10, 11:
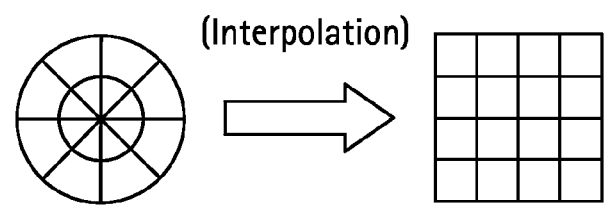
FIG. 10 shows transformation of an image through interpolation.
FIG. 11 lists a reconstruction time required by the method in accordance with the present invention in comparison with a reconstruction time required by a conventional method.

If iteration is recognized to be unnecessary at step 509, interpolation is performed at step 511. Since a reconstructed image is, as shown in the left of FIG. 10, an image composed of sector pixels, the image is transformed into an image composed of, as shown in the right of FIG. 10, rectangular pixels through the interpolation. As the interpolation, for example, bilinear interpolation is adopted. Consequently, an image can be transformed appropriately. However, the interpolation is not limited to the bilinear interpolation but may be performed using an appropriate algorithm.

FIG. 11 lists a time required for the foregoing image reconstruction in comparison with a time required for image reconstruction to be performed according to a conventional method. As listed in FIG. 11, when the method in accordance with the present invention is employed, a speed of image reconstruction increases to be approximately four to twenty times higher than a conventional speed.

Figure 12:
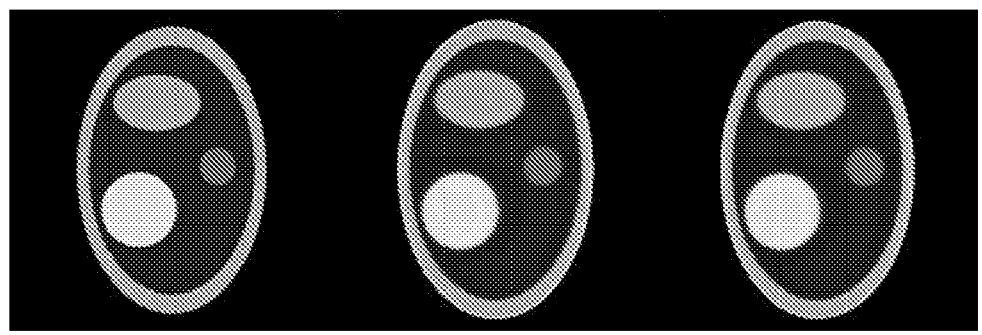
FIG. 12 includes halftone photographs showing a reconstructed image produced according to the method in accordance with the present invention in comparison with a reconstructed image produced according to the conventional method.

FIG. 12 shows a reconstructed image of a phantom produced according to a conventional method in comparison with a reconstructed image thereof produced according to the method in accordance with the present invention, (a) shows a real image of the phantom, (b) shows the reconstructed image produced according to the conventional method, and (c) shows the reconstructed image produced according to the method in accordance with the present invention. As apparent from FIG. 12, the method in accordance with the present invention provides the reconstructed image that is as good as the reconstructed image produced according to the conventional method.

Figure 13:
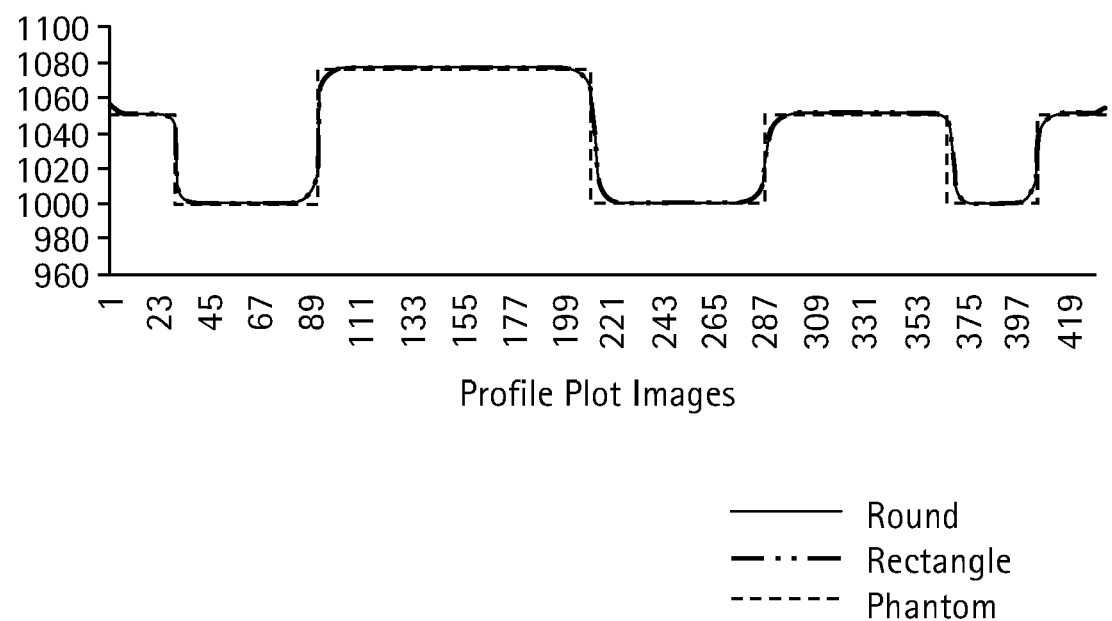
FIG. 13 shows a profile of the reconstructed image produced according to the method in accordance with the present invention in comparison with a profile of the reconstructed image produced according to the conventional method.

FIG. 13 shows one-dimensional profiles indicating the real image of the phantom and the reconstructed images produced according to the conventional method and the method in accordance with the present invention respectively. A dashed line depicts the profile of the real image of the phantom. An alternate long and two short dashes line depicts the profile of the reconstructed image produced according to the conventional method. A solid line depicts the profile of the reconstructed image produced according to the method in accordance with the present invention. The profiles of the reconstructed imaged produced according to the conventional method and the method in accordance with the present invention respectively have no difference. The alternate long and two short dashes line and solid line are fully superposed on each other.

Figure 14:
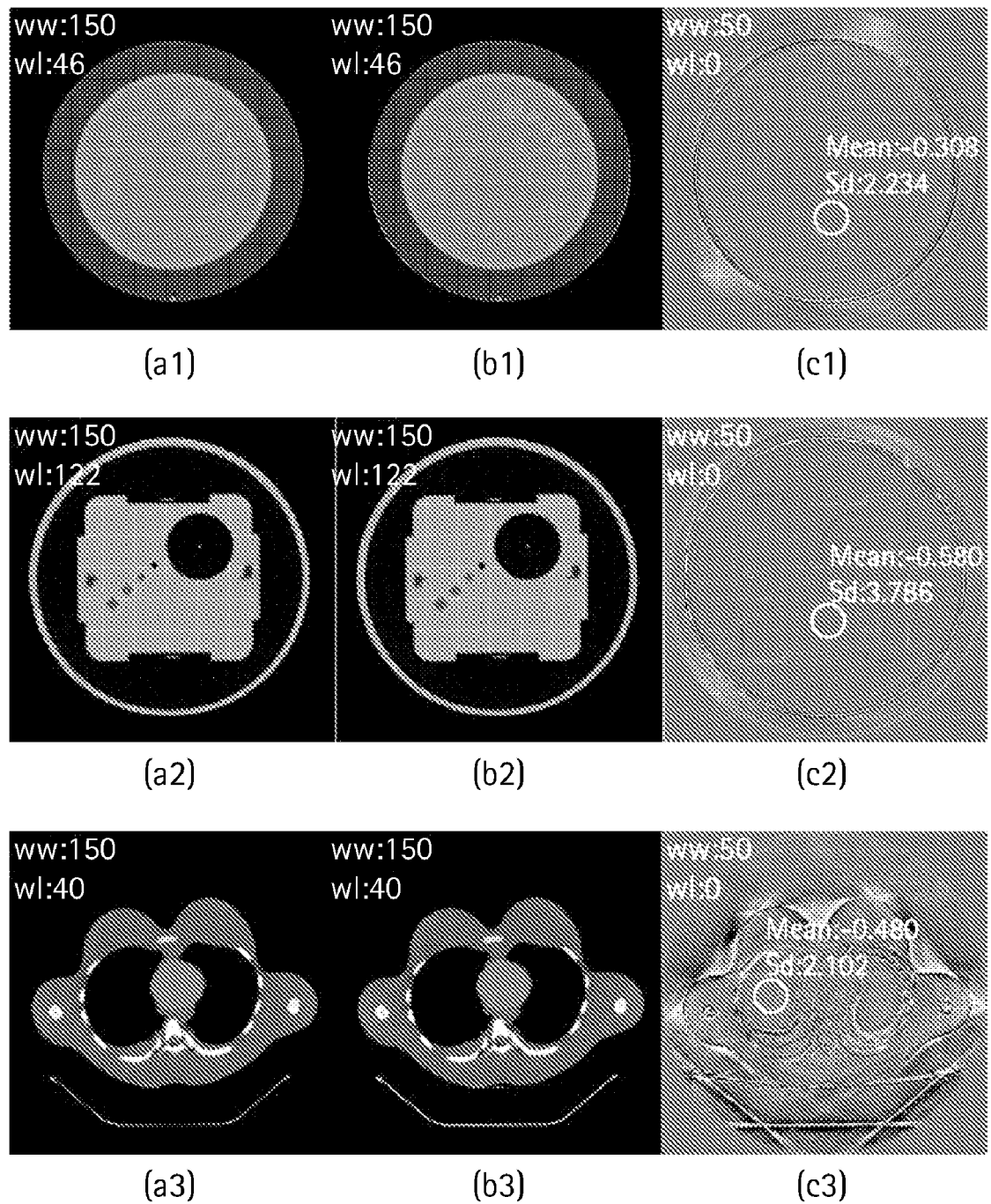
Figure 15A:
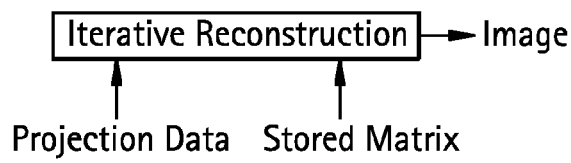
FIGS. 15a and 15b show processes employed in the conventional method.
Figure 15B:
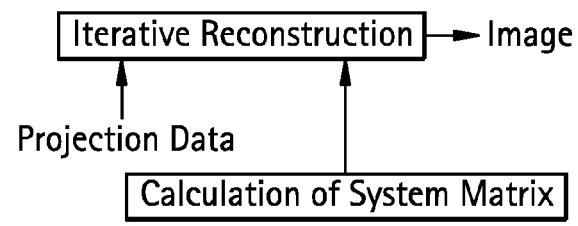

FIG. 14 shows reconstructed images of three phantoms produced according to the method in accordance with the present invention in comparison with reconstructed images thereof produced through filtered back projection (FBP). In FIG. 14, (*a*1), (*a*2), and (*a*3) show the reconstructed images produced through FBP, (b1), (b2), and (b3) show the reconstructed images produced according to the method in accordance with the present invention, and (c1), (c2), and (c3) show difference images. As apparent from FIG. 14, the method in accordance with the present invention provides images having nearly no difference from those produced through FBP.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus including data acquisition equipment that scans a subject with X-rays so as to acquire projection data, and image reconstruction equipment that reconstructs an image on the basis of the acquired projection data, wherein:
    the image reconstruction equipment comprises:
        a system model construction device for constructing a system model that has a plurality of concentric rings each segmented into a plurality of sectors;
        a system matrix construction device for constructing a system matrix associated with one view, by using some of all the sectors constituting the system model, the some of all the sectors being located on respective projection lines concerning the one view;
        a system matrix creation device for creating a system matrix associated with another view, by transforming the system matrix associated with the one view;
        an image reconstruction device that reconstructs an image through iterative reconstruction by using the system matrix and projection data; and
        a transformation device for transforming the image into an image composed of rectangular pixels.

2. The X-ray CT apparatus according to claim 1, wherein each of elements constituting the system matrix is a length of a projection line falling within each sector.

3. The X-ray CT apparatus according to claim 1, wherein each of elements constituting the system matrix is a partial area of a projection stripe falling within each sector.

4. The X-ray CT apparatus according to claim 3, wherein the partial area is a normalized area.

5. The X-ray CT apparatus according to claim 1, wherein the system matrix creation device creates a system matrix to be associated with another view at every time of iteration.

6. The X-ray CT apparatus according to claim 1, wherein an ordered subsets expectation maximization (OSEM) technique is adopted as the iterative reconstruction technique.

7. The X-ray CT apparatus according to claim 1, wherein the transformation device transforms an image into an image composed of rectangular pixels through bilinear interpolation.

8. The X-ray CT apparatus according to claim 1, wherein the projection lines express fan-beam X-rays.

9. The X-ray CT apparatus according to claim 1, wherein the projection lines express parallel-beam X-rays.

* * * * *